United States Patent [19]
Teng

[11] Patent Number: 6,015,887
[45] Date of Patent: Jan. 18, 2000

[54] CHIRAL PEPTIDE NUCLEIC ACIDS AND METHODS FOR PREPARING SAME

[75] Inventor: Kelly Teng, San Diego, Calif.

[73] Assignee: ISIS Pharmaceuticals, Inc., Carlsbad, Calif.

[21] Appl. No.: 08/843,034

[22] Filed: Apr. 11, 1997

[51] Int. Cl.[7] .............................. C12Q 1/68; C07H 21/02; C07H 21/04; A01N 43/04
[52] U.S. Cl. ........................... 536/23.1; 435/6; 536/24.1; 536/24.3; 536/24.31; 536/24.32; 536/24.33; 536/25.3; 536/25.31; 514/44
[58] Field of Search .................. 435/6; 514/44; 536/23.1, 25.3, 25.31, 24.1, 24.3, 24.31, 24.32, 24.33; 530/300, 333, 350

[56] References Cited

U.S. PATENT DOCUMENTS 5,539,082  7/1996  Nielsen et al. ........................ 530/300
5,705,333  1/1998  Shah et al. ................................ 435/6

FOREIGN PATENT DOCUMENTS

WO92/20702  11/1992  WIPO.

OTHER PUBLICATIONS

Burgess et al., "Solid Phase Syntheses of Oligoureas", *J. Am. Chem., Soc.,* 1997, 119, 1556–1564.

Dueholm et al., "Peptide Nucleic Acid (PNA) with a Chiral Backbone Based on Alanine", *Biomed. Med. Chem. Lett.,* 1994, 4(8), 1077–1080.

Dueholm et al., "An Efficient Synthesis of Boc–Aminoacetaldehyde and its Application to the Synthesis of N–(2–Boc–Aminoethyl) Glycine Esters", *Org. Prep. Proced. Int.,* 1993, 25(4), 457–461.

Egholm et al., "Peptide Nucleic Acids Containing Adenine or Guanine Recognize Thymine and Cytosine in Complementary DNA Sequences", *J. Chem. Soc., Chem. Commun.,* 1993, 800–801.

Egholm et al., "Peptide Nucleic Acids (PNA). Oligonucleotide Analogues with an Achiral Peptide Backbone", *J. Am. Chem. Soc.,* 1992, 114, 1895–1897.

Egholm et al., "Recognition of Guanine and Adenine in DNA by Cytosine and Thymine Containing Peptide Nucleic Acids (PNA)", *J. Am. Chem. Soc.,* 1992, 114, 9677–9678.

Egholm et al., "PNA hybridizes to complementary oligonucleotides obeying the Watson–Crick hydrogen–bonding rules", *Nature,* 1993, 365, 566–568.

Fukuyama et al., "2–and 4–Nitrobenzenesulfonamides: Exceptionally Versatile Means for Preparation of Secondary Amines and Protection of Amines", *Tetrahedron Lett.,* 1995, 36, 6373.

Greene and Wuts, Protective Groups in Organic Synthesis, 2d edition, John Wiley & Sons, New York, 1991.

Hanvey et al., "Antisense and Antigen Properties of Peptide Nucleic Acids", *Science,* 1992, 258, 1481–1485.

Helene et al., "Specific regulation of gene expression by antisense, sense and antigene nucleic acids", *Biochim. Biophys. Acta,* 1990, 1049, 99–125.

Hyrup et al., "Modification of the Binding Affinity of Peptide Nucleic Acids (PNA) . PNA with Extended Backbones consisting of 2–Aminoethyl–β–alanine or 3–Aminopropylglycine Units", *J. Chem. Soc., Chem. Commun.,* 1993, 518–519.

Kosynkina et al., "A Convenient Synthesis of Chiral Peptide Nucleic Acid (PNA) Monomers", *Tetra. Lett.,* 1994, 35 (29), 5173–5176.

(List continued on next page.)

*Primary Examiner*—Jezia Riley
*Attorney, Agent, or Firm*—Woodcock Washburn Kurtz Mackiewicz & Norris LLP

[57] ABSTRACT

Peptide nucleic acid monomers are provided having chirality in their backbones, as are synthetic methods therefor and peptide nucleic acid oligomers prepared therefrom.

42 Claims, 2 Drawing Sheets

OTHER PUBLICATIONS

Lagriffoul et al., "The Synthesis, Co–Oligomerization and Hybridization of a Thymine–Thymine Heterodimer Containing PNA",*Biomed. Med. Chem. Lett.*, 1994, 4 (8), 1081–1082.

Meltzer, "Peptide Nucleic Acids: Synthesis of Thymine, Adenine, Guanine, and Cytosine Nucleobases", *J. Org. Chem.*, 1995, 60, 4305–4308.

Mitsunobu, "The Use of Diethyl Azodicarboxylate and Triphenylphoshpine in Synthesis and Transformation of Natural Products", *Synthesis,* Jan. 1981, 1–28.

Nielsen et al., "Sequence–Selective Recognition of DNA by Strand Displacement with a Thymine–Substituted Polyamide", *Science,* 1991, 254, 1497–1500.

Nielsen et al., "Sequence specific inhibition of DNA restriction enzyme cleavage by PNA", *Nucl. Acids Res.,* 1993, 21(2), 197–200.

Orum et al., "Single base pair mutation analysis by PNA directed PCR clamping", *Nucl. Acids Res.,* 1993, 21(23), 5332–5336.

Uhlmann et al., "Antisense Oligonucleotides: A New Therapeutic Principle", Chem. Rev., 1990, 90(4), 544–584.

Teng et al.,*American Chemical Society,* Division of Medical Chemistry, 213th ACS National Meeting, San Francisco, CA, Apr. 13–17, 1997, 233.

glycinol

L-lysinol

D-lysinol glycine

L-alanine

L-leucine

D-glutamic acid

L-phenylalanine

L-tyrosine

L-lysine

D-lysine

CHIRAL PEPTIDE NUCLEIC ACIDS AND METHODS FOR PREPARING SAME

FIELD OF THE INVENTION

The present invention is directed to chiral peptide nucleic acids, to novel methods for preparing such compounds, and to synthetic intermediates employed in such methods.

BACKGROUND OF THE INVENTION

Oligonucleotides and their analogs have been developed and used in molecular biology in certain procedures as probes, primers, linkers, adapters, and gene fragments. Modifications to oligonucleotides used in these procedures include labeling with non isotopic labels, e.g. fluorescein, biotin, digoxigenin, alkaline phosphatase, or other reporter molecules.

Other modifications have been made to the ribose phosphate backbone to increase the nuclease stability of the resulting analog. These modifications include use of methyl phosphonates, phosphorothioates, phosphorodithioate linkages, and 2'-O-methyl ribose sugar units. Further modifications, include modifications made to modulate uptake and cellular distribution. Phosphorothioate oligonucleotides are presently being used as antisense agents in human clinical trials for various disease states including use as antiviral agents. With the success of these oligonucleotides for both diagnostic and therapeutic uses, there exists an ongoing demand for improved oligonucleotide analogs.

Oligonucleotides can interact with native DNA and RNA in several ways. One of these is duplex formation between an oligonucleotide and a single stranded nucleic acid. The other is triplex-formation between an oligonucleotide and double stranded DNA to form a triplex structure.

Peptide nucleic acids are compounds that in certain respects are similar to oligonucleotide analogs however in other very important respects their structure is very different. In peptide nucleic acids, the deoxyribose backbone of oligonucleotides has been replaced with a backbone more akin to a peptide than a sugar. Each subunit, or monomer, has a naturally occurring or non naturally occurring base attached to this backbone. One such backbone is constructed of repeating units of N-(2-aminoethyl)glycine linked through amide bonds. Because of the radical deviation from the deoxyribose backbone, these compounds were named peptide nucleic acids (PNAs).

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as determined by Tm's. This high thermal stability might be attributed to the lack of charge repulsion due to the neutral backbone in PNA. The neutral backbone of the PNA also results in the Tm's of PNA/DNA(RNA) duplex being practically independent of the salt concentration. Thus the PNA/DNA duplex interaction offers a further advantage over DNA/DNA duplex interactions which are highly dependent on ionic strength. Homopyrimidine PNAs have been shown to bind complementary DNA or RNA forming (PNA)2/DNA(RNA) triplexes of high thermal stability (see, e.g., Egholm, et al., Science, 1991, 254, 1497; Egholm, et al., J. Am. Chem. Soc., 1992, 114, 1895; Egholm, et al., J. Am. Chem. Soc., 1992, 114, 9677).

In addition to increased affinity, PNA has also been shown to bind to DNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are just the reverse with respect to the 5'-3' direction of the DNA or RNA.

PNAs bind to both single stranded DNA and double stranded DNA. As noted above, in binding to double stranded DNA it has been observed that two strands of PNA can bind to the DNA. While PNA/DNA duplexes are stable in the antiparallel configuration, it was previously believed that the parallel orientation is preferred for $(PNA)_2$/DNA triplexes.

The binding of two single stranded pyrimidine PNAs to a double stranded DNA has been shown to take place via strand displacement, rather than conventional triple helix formation as observed with triplexing oligonucleotides. When PNAs strand invade double stranded DNA, one strand of the DNA is displaced and forms a loop on the side of the $PNA_2$/DNA complex area. The other strand of the DNA is locked up in the $(PNA)_2$/DNA triplex structure. The loop area (alternately referenced as a D loop) being single stranded, is susceptible to cleavage by enzymes that can cleave single stranded DNA.

A further advantage of PNA compared to oligonucleotides is that their polyamide backbone (having appropriate nucleobases or other side chain groups attached thereto) is not recognized by either nucleases or proteases and are not cleaved. As a result PNAs are resistant to degradation by enzymes unlike nucleic acids and peptides.

Because of their properties, PNAs are known to be useful in a number of different areas. Since PNAs having stronger binding and greater specificity than oligonucleotides, they are used as probes in cloning, blotting procedures, and in applications such as fluorescence in situ hybridization (FISH). Homopyrimidine PNAs are used for strand displacement in homopurine targets. The restriction sites that overlap with or are adjacent to the D-loop will not be cleaved by restriction enzymes. Also, the local triplex inhibits gene transcription. Thus in binding of PNAs to specific restriction sites within a DNA fragment, cleavage at those sites can be inhibited. Advantage can be taken of this in cloning and subcloning procedures. Labeled PNAs are also used to directly map DNA molecules. In effecting this, PNA molecules having a fluorescent label are hybridized to complementary sequences in duplex DNA using strand invasion.

PNAs have further been used to detect point mutations in PCR-based assays (PCR clamping). PCR clamping uses PNA to detect point mutations in a PCR-based assay, e.g. the distinction between a common wild type allele and a mutant allele, in a segment of DNA under investigation. A PNA oligomer complementary to the wild type sequence is synthesized. The PCR reaction mixture contains this PNA and two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, one can determine the presence and exact identity of a mutant.

Considerable research is being directed to the application of oligonucleotides and oligonucleotide analogs that bind complementary DNA and RNA strands for use as diagnostics, research reagents and potential therapeutics. PCT/EP/01219 describes novel peptide nucleic acid (PNA) compounds which bind complementary DNA and RNA more tightly than the corresponding DNA. Because of these binding properties as well as their stability, such PNA compounds find many uses in diagnostics and research reagents uses associated with both DNA and RNA. With complementary DNA and RNA they can form double-stranded, helical structures mimicking doublestranded DNA, and they are capable of being derivatized to bear pendant groups to further enhance or modulate their binding, cellular uptake, or other activity.

Recent work in the field of chiral PNA monomers include research by Kosynkina, L., et al., *Tetrahedron Lett.*, 1994, 35, 5173–5176. Coupling of reactants to obtain oligoureas using protected amino acid derivatives is disclosed by Burgess, K., et al., *J. Am. Chem. Soc.*, 1997, 119, 1556–1564. A general method for the synthesis of Boc protected G,A,C and T PNA monomers is disclosed by Meltzer, P. C., *J. Org. Chem.*, 1995, 60, 4305–4308.

Monomers used to prepare PNAs, as well as the resultant PNAs, are typically in the form of racemic mixtures. It is expected, however, that enantiomerically pure oligomers will exhibit increased binding specificity as compared to racemic mixtures. Thus, such oligomers and compositions comprising them are greatly desired.

SUMMARY OF THE INVENTION

One aspect of the present invention provides a method for preparing compounds of formula (I):

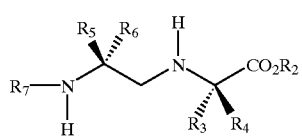

(I)

comprising providing an amine of formula (II):

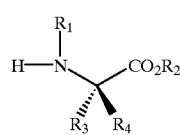

(II)

and contacting the amine with an alcohol of formula (III):

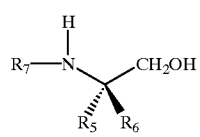

(III)

for a time and under conditions which effect dehydrative coupling thereof, wherein $R_1$ is a first amine protecting group, $R_2$ is a carboxyl protecting group, one of $R_3$ and $R_4$ is H and the other of $R_3$ and $R_4$ is a first amino acid side chain, one of $R_5$ and $R_6$ is H and the other of $R_5$ and $R_6$ is a second amino acid side chain, and $R_7$ is a second amine protecting group.

Compounds having formula (II) preferably are prepared by processes comprising the steps of appending a carboxyl protecting group to an amino acid, thereby producing a carboxyl-protected amino acid derivative, and then appending an amine protecting group to the carboxyl protected amino acid derivative. Compounds having formula (III) preferably are prepared by processes comprising the steps of appending an amine protecting group to an amino acid, thereby producing a amine-protected amino acid derivative, and reducing the carboxyl group thereof.

The present invention also provides compounds having formula (I), as well as PNA monomers prepared therefrom.

BRIEF DESCRIPTION OF THE FIGURES

The numerous objects and advantages of the present invention can be better understood by those skilled in the art by reference to the accompanying figures, in which.

DETAILED DESCRIPTION OF THE INVENTION

Figure 1:
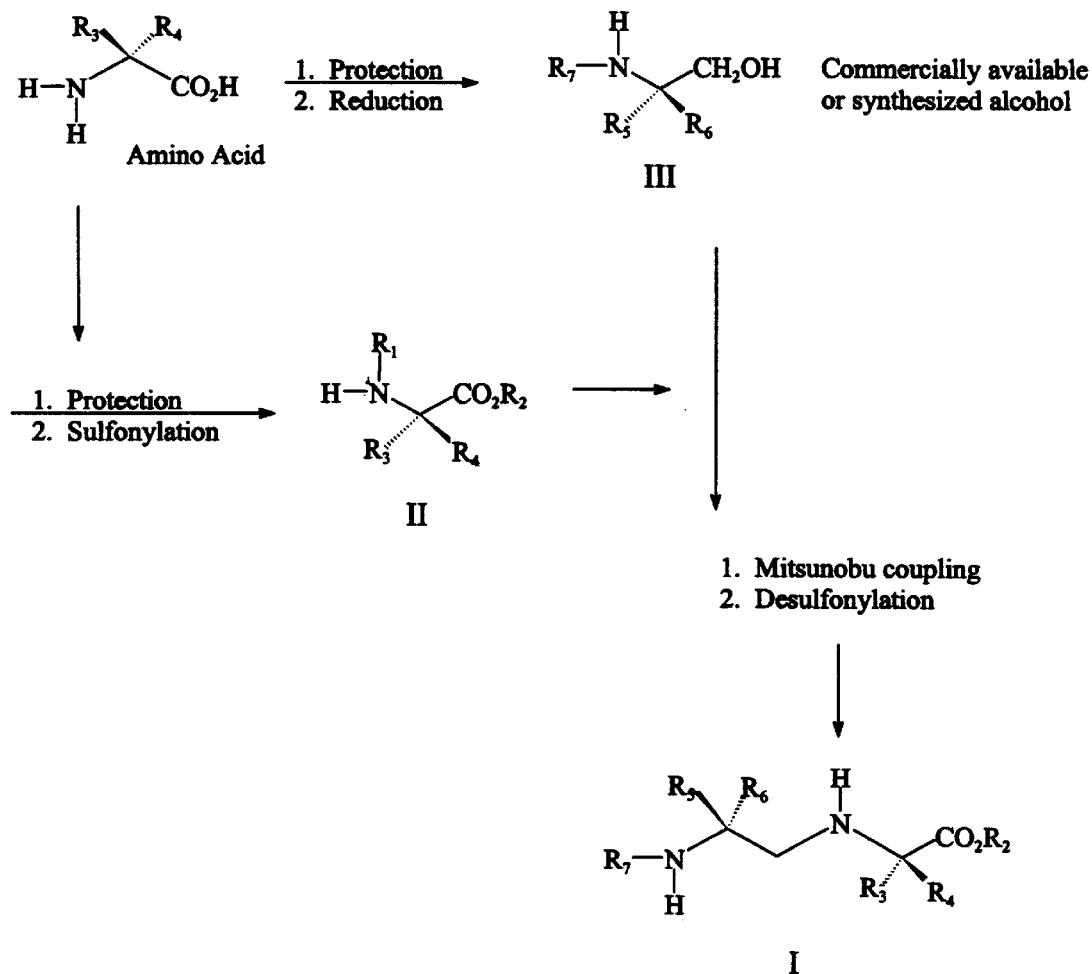
FIG. 1 shows a representative synthetic scheme for compounds having formula (I).
Figure 2:
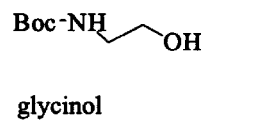
FIG. 2 shows certain protected amino acids according to the invention.
Figure 2:
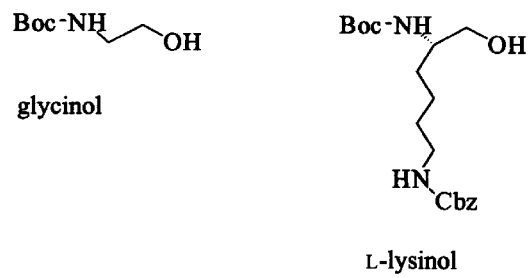
Figure 2:
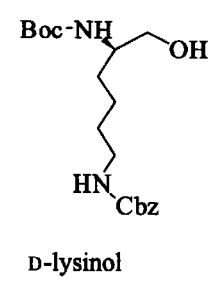
Figure 2:
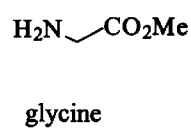
Figure 2:
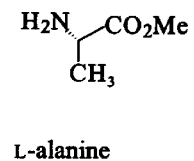
Figure 2:
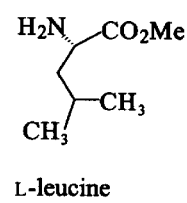
Figure 2:
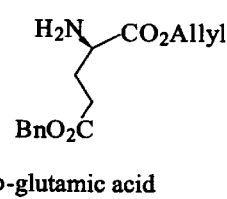
Figure 2:
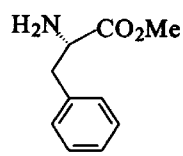
Figure 2:
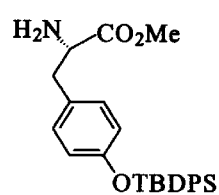
Figure 2:
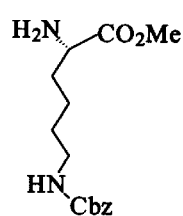
Figure 2:

Specific sequence recognition of DNA or RNA is of increasing importance for the development of biological probes and new reagents for use in research (Uhlmann, E., Peyman, A., *Chem. Rev.*, 1990, 90, 544, and Helene, C., Toulme, J. J., *Biochim. Biophys. Acta.*, 1990, 1049, 99). Peptide nucleic acid (PNA), an achiral analog of DNA where the nucleobases or nucleobase analogs are attached to a (2-aminoethyl)-glycine backbone through a methylene carbonyl linker have properties making them well suited for use as biological probes and other applications. PNA have shown strong binding affinity and specificity to complementary DNA, sequence specific inhibition of DNA restriction enzyme cleavage and site specific in vitro inhibition of translation (Egholm, M., et.al., *Chem. Soc., Chem. Commun.*, 1993, 800; Egholm, M., et.al., *Nature*, 1993, 365, 566; Nielsen, M., et.al. *Nucl. Acids Res.*, 1993, 21, 197; and Hanvey, J. C., et.al., *Science*, 1992, 258, 1481). Modifications of PNA include extended backbones (Hyrup, B., et.al. *Chem. Soc., Chem. Commun.*, 1993, 518), extended linkers between the backbone and the nucleobase, reversal of the amido bond (Lagriffoul, P. H., et.al., *Biomed. Chem. Lett.*, 1994, 4, 1081), and the use of a chiral backbone based on alanine (Dueholm, K. L, et.al., *BioMed. Chem. Lett.*, 1994, 4, 1077).

This invention is directed to a modification of PNA that has increased specificity while maintaining comparable affinity. This is achieved through the use of 2-aminoethyl-based monomers having chiral Cα-positions (i.e., the carbon atoms in compound (I) to which $R_3$ and $R_4$ are bound) and/or Cβ-positions (i.e., the carbon atoms in compound (I) to which $R_5$ and $R_6$ are bound). As will be recognized such monomers can have SS, RR, SR, or RS configuration. Chiral monomers according to the invention are those wherein there is 100% stereochemical purity with respect to the Cα-position and/or the Cβ-position when naturally occurring amino acids are used in the synthesis. Purity of the Cα- and Cβ-positions is determined by the purity of the amino acid starting materials and not a function of the coupling procedure. It is also envisioned within the scope of the present invention that other than naturally occurring amino acids may be used to prepare 2-aminoethyl-based monomers. It is preferred that chiral PNA oligomers, in turn, are those wherein the stereochemical purity with respect to the Cα- and/or Cβ-positions of at least one 2-aminoethyl-based monomer is at least 75%. It is preferred that at least three of such units exhibit these levels of stereochemical purity in a PNA oligomer, and particularly preferred that at least one of the units exhibit these purity levels.

Preferred peptide nucleic acid monomers of the invention have formula (IV):

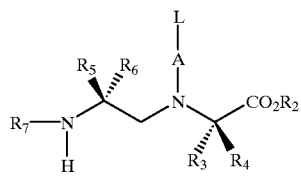
(IV)

wherein:
R$_2$ is a carboxyl protecting group;
one of R$_3$ and R$_4$ is H and the other of R$_3$ and R$_4$ is an amino acid side chain;
one of R$_5$ and R$_6$ is H and the other of R$_5$ and R$_6$ is an amino acid side chain;
R$_7$ is a second amine protecting group;
L is selected from the group consisting of hydrogen, hydroxy, (C$_1$–C$_4$)alkanoyl, naturally occurring nucleobases, non-naturally occurring nucleobases, aromatic moieties, DNA intercalators, nucleobase-binding groups, and heterocyclic moieties, reporter ligands, wherein amino groups are, optionally, protected by amino protecting groups;

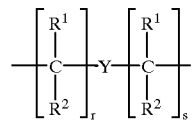
(IIa)

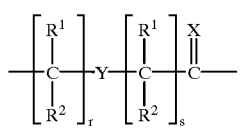
(IIb)

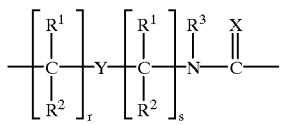
(IIc)

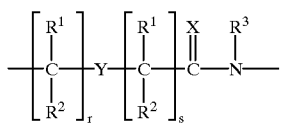
(IId)

where:

X is O, S, Se, Nr$^3$, CH$_2$ or C(CH$_3$)$_2$;

Y is a single bond, O, S or NR$^4$ where R$^4$ is as described above;

each r and s is zero or an integer from 1 to 5;

each R$_1$ and R$_2$ is independently selected from the group consisting of hydrogen, (C$_1$–C$_4$)alkyl which may be hydroxy- or alkoxy- or alkylthio-substituted, hydroxy, alkoxy, alkylthio, amino and halogen; and R$^3$ is selected from the group consisting of hydrogen, (C$_1$–C$_4$)alkyl, hydroxy- or alkoxy- or alkylthio-substituted (C$_1$–C$_4$)alkyl, hydroxy, alkoxy, alkylthio and amino.

Alkyl groups according to the invention include but are not limited to straight chain, branched chain, and cyclic hydrocarbons such as methyl, ethyl, propyl, pentyl, isopropyl, 2-butyl, isobutyl, 2-methylbutyl, and isopentyl moieties having 1 to about 12 carbon atoms, preferably 1 to about 7 carbon atoms.

The term amino acid as used herein is intended to include all naturally-occurring and synthetic amino acids known in the art. In general, amino acids have structure H$_2$N—CH(R$_C$)—C(O)OH where R$_C$ is the amino acid side chain. Representative, naturally-occurring side chains are shown in Table 1.

TABLE 1

| | |
|---|---|
| CH$_3$— | CH$_3$—CH$_2$—S—CH$_2$—CH$_2$— |
| HO—CH$_2$— | HO—CH$_2$—CH$_2$— |
| C$_6$H$_5$—CH$_2$— | CH$_3$—CH$_2$(OH) — |
| HO—C$_6$H$_5$—CH$_2$— | HO$_2$C—CH$_2$—NH$_2$C(O)—CH$_2$— |

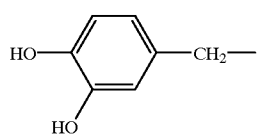
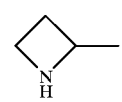

TABLE 1-continued

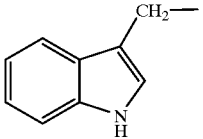

HCO$_2$—CH$_2$—CH$_2$—
NH$_2$C(O)—CH$_2$—CH$_2$—
(CH$_3$)$_2$—CH—
(CH$_3$)$_2$—CH—CH$_2$—
CH$_3$—CH$_2$—CH$_2$—

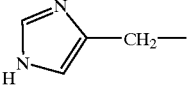

H$_2$N—CH$_2$—CH$_2$—CH$_2$—
H$_2$N—C(NH)—NH—CH$_2$—CH$_2$—CH$_2$—
H$_2$N—C(O)—NH—CH$_2$—CH$_2$—CH$_2$—
CH$_3$—CH$_2$—CH(CH$_3$)—

HS—CH$_2$—
HO$_2$C—CH(NH$_2$)—CH$_2$—S—S—CH$_2$—
CH$_3$—CH$_2$—
CH$_3$—S—CH$_2$—CH$_2$—

CH$_3$—CH$_2$—CH$_2$—CH$_2$—
H$_2$N—CH$_2$—CH$_2$—CH$_2$—CH$_2$—

---

Preferred side chains include those that exhibit polarity such as those having primary or secondary amines. A more preferred list includes HO—CH$_2$—, HO—C$_6$H$_5$—CH$_2$—, HO$_2$C—CH(NH$_2$)—CH$_2$—S—S—CH$_2$—, HO—CH$_2$—CH$_2$—, HCO$_2$—CH$_2$—CH$_2$—, H$_2$N—C(NH)—NH—CH$_2$—CH$_2$—CH$_2$—, H$_2$N—C(O)—NH—CH$_2$—CH$_2$—CH$_2$—, H$_2$N—CH$_2$—CH$_2$—CH$_2$—CH$_2$— and p—HO—m—HO—C$_6$H$_4$—CH$_2$—.

Monomers having formula (IV) preferably are prepared by functionalizing amine compounds having formula (I):

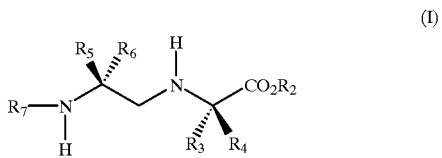

(I)

These amine compounds, in turn, are prepared by reacting an amine- and carboxyl-protected compound of formula (II):

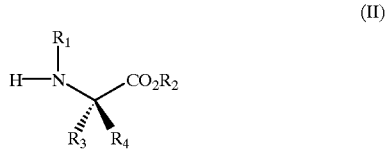

(II)

with an amine-protected alcohol of formula (III):

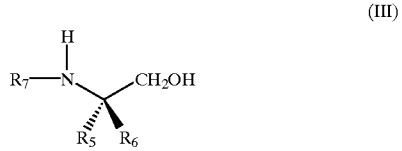

(III)

for a time and under conditions which effect dehydrative coupling through the free amine and alcohol functionalities thereof. Such coupling reactions can be effected by using standard procedures and methods as is known in the art for the coupling of peptides. In preferred embodiments, coupling is effected in an aprotic solvent, e.g. THF in the presence of a triaryl phosphine (e.g., triphenyl phosphine) and a dialkyl azodicarboxylate (e.g., diethyl azodicarboxylate; "DEAD") in accordance with the so-called Mitsunobu procedures (see, e.g., Mitsunobu, *Synthesis*, January 1–28, 1981.

As shown in FIG. 1, compounds having formula (II) preferably are prepared by methods wherein amino acids (6) are protected with suitable carboxyl groups. Protecting groups are known per se as chemical functional groups that can be selectively appended to and removed from functionality, such as amine, carboxyl, or hydroxyl groups, which present in a chemical compound, thus rendering such functionality inert to chemical reaction conditions to which the compound is exposed. See, e.g., Greene and Wuts, Protective Groups in Organic Synthesis, 2d edition, John Wiley & Sons, New York, 1991. Representative carboxyl protecting groups include lower (i.e., $C_1$–$C_7$) alkyl esters, benzyl esters, and phenyl esters including pentafluorophenyl and p-nitrophenyl. Preferred carboxyl protecting groups are those that are stable to standard Mitsunobu coupling procedures (Mitsunobu, ibid) illustrated in Example 10 below but can be removed using Pd(0), base hydrolysis, F$^-$, or β-elimination conditions.

Carboxyl-protected derivatives of amino acids (6) are further reacted to protect amino groups therein and, thus, form amine compounds having formula (II). Representative amine protective groups for such procedures include alkyl-, arylsulfonyl, CF$_3$SO$_2$ and acyl groups, with aryl sulfonyl groups such as nitrobenzyl sulfonyl and o- or p-nitrobenzyl sulfonyl groups being particularly preferred. Preferred amine protecting groups are those that are stable to Mitsunobu coupling procedures but can be removed under conditions utilizing reagent mixtures such as PhSH/K$_2$CO$_3$/DMF or conditions such as used by Fukuyama, T., Jow, C. K., *Tetrahedron Lett.*, 1995, 36, 6373.

Compounds having formula (III) preferably are prepared by appending amine protecting groups directly to amino acids followed by reduction of the carboxyl group to a primary alcohol. Suitable protecting groups in this regard include the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. A more representative group includes o-nitrophenylsulfenyl (Nps), 6-nitroveatryloxycarbonyl (NVOC), 2-trimethylsilylethoxycarbonyl (Teoc), Pent-4-enoyl, photolysis and Br$_2$/H$_2$O. Preferred amine protecting groups for direct attachment to amino acids are those that are stable to Mitsunobu coupling procedures but can be removed with reagents such as trifluoroacetic acid, base, Pd, hydrogenation and HF.

In accordance with the invention, amine-protected derivatives of amino acids are exposed to reaction conditions to reduce carboxyl functionality therein and, thereby, produce alcohols having formula (III). A variety of reactions conditions for effecting such reduction are well-known to those skilled in the art. Representative reaction conditions include hydride reductions. In preferred embodiments, reduction is effected using $NaBH_4$ or $BH_3/Me_2S$.

PNA oligomers comprising at least one chiral monomer are prepared in accordance with methods known to those skilled in the art (see, e.g., U.S. Pat. No. 5,539,082, the contents of which are incorporated herein by reference). Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention. Preferably, the PNA oligomer is prepared to be complementary to a target molecule, i.e., at least a portion of the PNA oligomer has the ability to hybridize due to Watson-Crick base pair attraction to the target molecule.

The thermal stability of homopyrimidine PNA/DNA and homopyrimidine PNA*/DNA wherein PNA* denotes a PNA oligomer containing one chiral (SS or RR) monomer was studied to determine the effects of the chiral monomer on the Tm. It has been previously shown that a homothymine PNA decamer forms a very stable 2:1 complex with its complementary DNA. Introduction of one mismatch in the DNA strand resulted in a significant destabilization of the PNA/DNA complex. When the SS isomer H-TTTTTTTTTT-Lys-$NH_2$ (where T denotes the SS monomer, N-(2S-Boc-aminocyclohex-1S-yl)-N-(thymin-1-ylacetyl)glycine) was hybridized with the DNA 10mer $A_{10}$, the Tm was comparable to that of the PNA(H-TTTTTTTTTT-Lys-$NH_2$)/DNA complex. Introduction of a mismatch in the DNA 10mer corresponding to the position of the chiral SS monomer in the chiral PNA 10mer resulted in the same destabilization as the PNA without a chiral monomer present. The results of this study show that the 10mer containing the SS isomer shows comparable binding affinity and equivalent specificity when compared to the 10mer PNA without the SS isomer.

When the same thermal stability studies were performed on the RR isomer, N-(2R-Boc-aminocyclohex-1R-yl)-N-(thymin-1-ylacetyl)-glycine, there was seen poor binding affinity as well as poor specificity.

Oligomers of the present invention are useful as research reagents and as diagnostic tools. PNAs have been used in studies to discriminate between fully complementary and single base mismatch targets (Orum, H., et.al., *Nucleic Acids Research*, 1993, 21, 5332–5336). The method utilizes the properties of PNA e.g. higher thermal stability, greater specificity when bound to complementary nucleic acid sequences than the corresponding deoxyribooligonucleotides and that PNAs are not recognized by DNA polymerase as primers. A PNA/DNA complex can effectively block the formation of a PCR product when the PNA is targeted against the PCR primer site. This method is effective in blocking target sequences when two target sequences in the same assay differ by only one base pair. Compounds of the present invention having greater specificity than normal PNA are well suited for use in diagnostic assays of this type. In preferred embodiments, it is preferred that at least one PNA monomer having a chiral center in the ethyl portion of the monomer is incorporated into the PNA oligomer at the site where a mismatch (i.e. variability of the target molecule) is expected or known to occur.

PNA oligomers having at least one chiral monomer are easily tagged with fluorescein or rhodamine using an aminohexanoic linking moiety. These tagged PNA oligomers are well suited for use as probes for a section of DNA of interest. Many other types of labeling reagents and linking moieties are amenable to the present invention.

The following examples are merely illustrative of the present invention and should not be considered limiting of the scope of the invention in any way. These examples and equivalents thereof will become more apparent to those skilled in the art in light of the present disclosure and the accompanying claims. The disclosures of each patent, patent application, and publication cited or described in this document are hereby incorporated herein by reference in their entirety.

EXAMPLE 1

Protection of the Hydroxyl Group of L-tyrosine, Synthesis of O-(tert-Butyldiphenylsilyl)-L-tyrosine methyl ester (1)

To a solution of L-tyrosine methyl ester (Sigma Chemical Company) (10.0 g, 51.3 mmol) and diisopropylethylamine (25.9 g, 200.0 mmol) in $CH_2Cl_2$ (400 mL) was added t-butyldiphenylsilyl chloride (TBDPS-Cl; 35.2 g, 128.2 mmol) at 23° C. The resultant mixture was stirred at 23° C. for 14 hours. The crude reaction mixture was dried over ($MgSO_4$) and concentrated in vacuo. The resultant residue was purified by silica gel flash column chromatography. The polarity of the eluting solvent mixture was adjusted according to the $R_f$ value of the product. The eluted fractions were combined, dried over $MgSO_4$, concentrated and dried to give 19.5 g (87.8% yield) of O-(tert-butyldiphenylsilyl)-L-tyrosine methyl ester as a colorless syrup. $R_f$(hexanes/ethyl acetate (AcOEt)/methanol (MeOH) 20:20:1)=0.38.

$^1$H NMR was performed, resulting in the following peaks: δ1.09 (s, 9H), 1.53 (s, 2H, $D_2O$ exchangable), 2.72 (dd, 1H, J=13.6, 7.8 Hz), 2.94 (dd, 1H, J=13.6, 5.3 Hz), 3.62 (dd, 1H, J=7.8, 5.3 Hz), 3.65 (s, 3H), 6.67–6.72 (m, 2H), 6.85–6.92 (m, 2H), 7.30–7.46 (m, 6H), 7.67–7.72 (m, 4H). $^{13}$C NMR was also performed, resulting in the following peaks: δ26.53, 40.35, 55.85, 119.75, 127.72, 129.54, 129.85, 129.98, 132.94, 135.49, 154.48, 175.38.

EXAMPLE 2

Protection of the α-carboxyl Group of Boc-D-glutamic acid γ-benzyl ester, Synthesis of Boc-D-glutamic acid α-allyl-γ-benzyl diester (2)

A suspension of Boc-D-glutamic acid γ-benzyl ester (25.0 g, 75.0 mmol; Advanced ChemTech, CAT# BE3235) and $K_2CO_3$ (20.7 g, 150.0 mmol) in DMF (150 mL) was added allyl bromide (18.1 g, 150.0 mmol). The reaction was stirred at 23° C. for 2 hours. The resultant mixture was diluted with ethyl acetate (500 mL), and washed with $H_2O$ (2×500 mL). The crude reaction mixture was dried over ($MgSO_4$) and concentrated in vacuo. The resultant residue was purified by silica gel flash column chromatography. The polarity of the eluting solvent mixture was adjusted according to the $R_f$ value of the product. $R_f$(hexanes/AcOEt 1:1) 0.62. The Boc-D-glutamic acid α-allyl-γ-benzyl diester (24.4 g; 87.5% yield) was obtained as a white solid.

Melting point (mp) was 58–61° C. $^1$H NMR: δ1.44 (s, 9H), 1.84–2.07 (m, 1H), 2.14–2.32 (m, 1H), 2.47 (ddd, 2H, J=9.7, 6.8, 2.0 Hz), 4.36 (m, 1H), 4.61 (ddd, 1H, J=5.7, 3.0, 1.3 Hz), 4.64 (ddd, 1H, J=4.5, 1.6, 1.2 Hz), 5.10 (br s, 1H), 5.12 (s, 2H), 5.25 (ddd, 1H, J=11.6, 1.6, 1.2 Hz), 5.33 (ddd, 1H, J=16.2, 3.0, 1.6 Hz), 5.90 (dddd, 1H, J=16.2, 11.6, 5.7, 4.5 Hz), 7.35 (s, 5H). $^{13}$C NMR: δ27.68, 28.31, 30.33, 53.00, 65.96, 66.46, 79.93, 118.84, 127.69, 127.7, 128.25, 128.57, 131.59, 135.84, 148.01, 155.40, 171.89, 172.49.

EXAMPLE 3

Synthesis of N-(o-nitrosulfonyl)glycine methyl ester (3)

To a solution of a glycine methyl ester (Sigma Chemical Company) (25.0 mmol) and diisopropylethylamine (6.5 g, 50.0 mmol) in $CH_2Cl_2$ (200 mL) was added 2-nitrobenzenesulfonyl chloride (6.7 g, 30.0 mmol) at 0° C. over 0.5 hours. The reaction was very exothermic. The reaction mixture was warmed up to 23° C. and stirred for an additional 2 hours. The resultant mixture was diluted with EtOAc (500 mL) and washed with $H_2O$ (2×250 mL). The crude reaction mixture was dried over ($MgSO_4$) and concentrated in vacuo. The resultant residue was purified by silica gel flash column chromatography. The polarity of the eluting solvent mixture was adjusted according to the $R_f$ value of the product. The N-(o-nitrosulfonyl)glycine methyl ester (98.5% yield) was obtained as a white solid.

mp: 111–2° C. $R_f(CH_2Cl_2/AcOEt$ 9:1) 0.63. $^1$H NMR: δ3.61 (s, 3H), 4.02 (d, 2H, J=5.8 Hz), 6.05 (t, 1H, J=5.8 Hz), 7.72–7.76 (m, 2H), 7.92–7.97 (m, 1H), 8.07–8.12 (m, 1H). $^{13}$C NMR: δ44.78, 52.56, 125.63, 130.63, 132.97, 133.80, 147.78, 169.07. Anal Calcd for $C_9H_{10}N_2O_6S$: C, 39.42; H, 3.65; N, 10.22. Found: C, 39.48; H, 3.62; N,10.24.

EXAMPLE 4

Synthesis of N-(o-nitrosulfonyl)L-alanine methyl ester (4)

L-Alanine methyl ester (Aldrich Chemical Company) (25.0 mmol) was treated as per the procedure of Example 3 to give N-(o-nitrosulfonyl)L-alanine methyl ester (93.0%) as a white solid. mp: 72–4° C. $R_f(CH_2Cl_2/AcOEt$ 9:1) 0.74. $^1$H NMR: δ1.49 (d, 3H, J=7.2 Hz), 3.52 (s, 3H), 4.25 (dq, 1H, J=8.3, 7.2 Hz), 6.01 (d, 1H, J=8.3 Hz), 7.72–7.76 (m, 2H), 7.92–7.97 (m, 1H), 8.07–8.12 (m, 1H). $^{13}$C NMR: δ19.41, 52.39, 52.56, 125.51, 130.48, 133.11, 133.73, 134.04, 147.59, 171.99.

EXAMPLE 5

Synthesis of N-(o-nitrosulfonyl)L-leucine methyl ester (5)

L-Leucine methyl ester (Sigma Chemical Company) (25.0 mmol) was treated as per the procedure of Example 3 to give N-(o-nitrosulfonyl)L-leucine methyl ester (94.6%) as a pale yellow syrup. $R_f(CH_2Cl_2/AcOEt$ 9:1): 0.78. $^1$H NMR: δ0.94 (d, 6H, J=6.6 Hz), 1.60 (dd, 2H, J=7.5, 6.9 Hz), 1.82 (tq, 1H, J=7.5, 6.6 Hz), 3.41 (s, 3H), 4.20 (dt, 1H, J=9.7, 7.5 Hz), 5.95 (d, 1H, J=9.7 Hz), 7.72–7.76 (m, 2H), 7.92–7.97 (m, 1H), 8.07–8.12 (m, 1H). $^{13}$C NMR: δ21.23, 22.62, 24.29, 41.68, 52.21, 55.33, 125.43, 130.38, 133.00, 133.64, 134.02, 147.54, 171.92.

EXAMPLE 6

Synthesis of Nα-(o-nitrosulfonyl)Nε-Cbz-L-lysine methyl ester (6)

Nε-Cbz-L-lysine methyl ester (Sigma Chemical Company) (25.0 mmol) was treated as per the procedure of Example 3 to give Nα-(o-nitrosulfonyl)Nε-Cbz-L-lysine methyl ester (94.0%) as a yellow syrup. $R_f(CH_2Cl_2/AcOEt$ 9:1): 0.47. $^1$H NMR: δ1.40–1.55 (m, 4H), 1.70–1.95 (m, 2H), 3.17 (m, 2H), 3.47 (s, 3H), 4.16 (dt, 1H, J=9.3, 5.3 Hz), 4.79 (br s, 1H), 5.11 (s, 2H), 6.13 (d, 1H, J=9.3 Hz), 7.26–7.40 (m, 5H), 7.69–7.74 (m, 2H), 7.88–8.03 (m, 1H), 8.05–8.08 (m, 1H). $^{13}$C NMR: δ22.19, 29.17, 32.49, 40.51, 52.44, 56.58, 66.59, 125.52, 128.04, 130.47, 132.89, 133.80, 136.75, 147.65, 156.59, 171.49. Anal Calcd for $C_{21}H_{25}N_3O_8S$ (0.2 $CHCl_3$): C, 50.59; H, 5.01; N, 8.35. Found: C, 50.51; H, 4.96; N, 8.17.

EXAMPLE 7

Synthesis of Nα-(o-nitrosulfonyl)Nε-Cbz-D-lysine methyl ester (7)

Nε-Cbz-D-lysine methyl ester (Sigma Chemical Company) (25.0 mmol) was treated as per the procedure of Example 3 to give Nα-(o-nitrosulfonyl)Nε-Cbz-D-lysine methyl ester (94.1%) as a yellow syrup.

EXAMPLE 8

Synthesis of Nα-(o-nitrosulfonyl)L-phenylalanine methyl ester (8)

L-Phenylalanine methyl ester (Sigma Chemical Company) (25.0 mmol) was treated as per the procedure of Example 3 to give Nα-(o-nitrosulfonyl)L-phenylalanine methyl ester (95.9%) as a yellow solid. mp: 82–4° C. $R_f(CH_2Cl_2/AcOEt$ 9:1) 0.62. $^1$H NMR: δ3.07 (dd, 1H, J=13.8, 6.8 Hz), 3.17 (dd, 1H, J=13.8, 6.8 Hz), 3.52 (s, 3H), 4.47 (dt, 1H, J=8.3, 6.8 Hz), 6.01 (d, 1H, J=8.3 Hz), 7.08–7.28 (m, 5H), 7.63–7.70 (m, 2H), 7.82–7.88 (m, 1H), 7.94–7.99 (m, 1H). $^{13}$C NMR: δ39.13, 52.50, 57.91, 125.57, 127.41, 127.73, 128.68, 129.30, 130.32, 133.03, 133.67, 133.99, 134.99, 147.43, 170.87. Anal Calcd for $C_{16}H_{16}N_2O_6S$: C, 52.75; H, 4.40; N, 7.69. Found: C, 52.77; H, 4.47; N, 7.61.

EXAMPLE 9

Synthesis of Nα-(o-nitrosulfonyl)O-(tert-butyldiphenylsilyl)-L-tyrosine methyl ester (9)

O-(tert-Butyldiphenylsilyl)-L-tyrosine methyl ester (synthesized in Example 1) (1) (25.0 mmol) was treated as per the procedure of Example 3 to give Nα-(o-nitrosulfonyl) O-(tert-butyldiphenylsilyl)-L-tyrosine methyl ester (99.2%) as a yellow foam. $R_f$(hexanes/AcOEt 1:1) 0.61. $^1$H NMR: δ1.09 (s, 9H), 2.97(d, 2H, J=6.2 Hz), 3.42 (s, 3H), 4.35 (t, 1H, J=6.2 Hz), 5.95 (br s, 1H), 6.59–6.67 (m, 2H), 6.77–6.83 (m, 2H), 7.31–7.46 (m, 6H), 7.58–7.70 (m, 6H), 7.75–7.84 (m, 1H), 7.94–7.99 (m, 1H). $^{13}$C NMR: δ19.55, 26.68, 38.44, 52.33, 57.94, 120.05, 125.50, 127.45, 127.72, 127.91, 130.09, 130.18, 130.38, 132.94, 133.66, 134.10, 135.60, 147.57, 154.99, 170.88. Anal Calcd for $C_{32}H_{34}N_2O_7SSi$ (0.7$H_2$)): C, 60.89; H, 5.61; N, 4.44. Found: C, 60.86; H, 5.51; N, 4.35.

EXAMPLE 10

Mitsunobu Coupling, Synthesis of N-(N-Boc-aminoethyl)-N-(o-nitrosulfonyl)glycine methyl ester (10)

To a solution of N-(o-nitrosulfonyl)glycine methyl ester (3) (20.0 mmol), N-Boc-aminoethanol (3.9 g, 24.0 mmol) (Aldrich Chemical Company), and $Ph_3P$ (8.8 g, 33.6 mmol)

in THF (150 mL) was added DEAD (4.9 g, 28.0 mmol) at 0° C. The mixture was warmed up to 23° C. and stirred for 14 hours. The resultant mixture was concentrated at reduced pressure and the residue was redissolved in hexanes/AcOEt (1:1, 200 mL). After standing at 23° C. for 14 hours, the precipitate (EtO$_2$CNH—NHCO$_2$Et) was removed by suction filtration. The filrate was concentrated at reduced pressure and the residue was purified by silica gel flash column chromatography to give a 97.1% yield of N-(N-Boc-aminoethyl)-N-(o-nitrosulfonyl)glycine methyl ester as a white foam. R$_f$(CH$_2$Cl$_2$/AcOEt 9:1): 0.36. $^1$H NMR: δ1.42 (s, 9H), 3.30 (m, 2H), 3.50 (m, 2H), 3.67 (s, 3H), 4.22 (s, 2H), 5.04 (br s, 1H), 7.72–7.76 (m, 2H), 7.92–7.97 (m, 1H), 8.07–8.12 (m, 1H). $^{13}$C NMR: δ28.16, 38.27, 48.44, 52.19, 79.18, 124.05, 130.59, 131.89, 132.50, 133.86, 147.69, 155.91, 169.41. Anal Calcd for C$_{16}$H$_{23}$N$_3$O$_8$S: C, 46.04; H, 5.52; N, 10.07. Found: C, 46.01; H, 5.44; N, 10.01.

EXAMPLE 11

Mitsunobu Coupling, Synthesis of N-(N-Boc-aminoethyl)-N-(o-nitrosulfonyl)L-alanine methyl ester (11)

A solution of N-(o-nitrosulfonyl)L-alanine methyl ester (20.0 mmol) was treated as per the procedure of Example 10 to give a 91.5% yield of N-(N-Boc-aminoethyl)-N-(o-nitrosulfonyl)L-alanine methyl ester as a yellow syrup. R$_f$(CH$_2$Cl$_2$/AcOEt 9:1) 0.45. $^1$H NMR: δ1.42 (s, 9H), 1.55 (d, 3H, J=7.4 Hz), 3.33 (m, 4H), 3.59 (s, 3H), 4.76 (q, 1H, J=7.4 Hz), 5.12 (br s, 1H), 7.56–7.70 (m, 3H), 8.01–8.05 (m, 1H). $^{13}$C NMR: δ28.16, 38.27, 48.44, 52.19, 79.18, 124.05, 130.59, 131.89, 132.50, 133.86, 147.69, 155.91, 169.41. Anal Calcd for C$_{17}$H$_{25}$N$_3$O$_8$S: C, 47.33; H, 5.80; N, 9.74. Found: C, 47.65; H, 5.53; N, 9.81.

EXAMPLE 12

Mitsunobu Coupling, Synthesis of N-(N-Boc-aminoethyl)-N-(o-nitrosulfonyl)L-leucine methyl ester (12)

A solution of N-(o-nitrosulfonyl)L-leucine methyl ester (5) (20.0 mmol) was treated as per the procedure of Example 10 to give a 93.4% yield of N-(N-Boc-aminoethyl)-N-(o-nitrosulfonyl)L-leucine methyl ester as a yellow syrup. R$_f$(CH$_2$Cl$_2$/AcOEt 9:1) 0.60. $^1$H NMR: δ0.96 (d, 3H, j=5.5 Hz), 0.99 (d, 3H, j=5.5 Hz), 1.44 (s, 9H), 1.75 (m, 2H), 3.37 (m, 4H), 3.54 (s, 3H), 4.67 (t, 1H, j=7.1 Hz), 5.02 (br s, 1H), 5.02 (br s 1H), 7.56–7.70 (m, 3H), 8.01–8.05 (m, 1H). $^{13}$C NMR: δ21.05, 22.80, 24.45, 28.36, 38.84, 40.99, 45.91, 52.17, 59.01, 79.21, 123.91, 130.96, 131.53, 131.78, 133.94, 148.09, 155.93, 171.56. Anal Calcd for C$_{20}$H$_{31}$N$_3$O$_8$S: C, 50.74; H, 6.56; N, 8.88. Found: C, 50.65; H, 6.35; N, 8.87.

EXAMPLE 13

Mitsunobu Coupling, Synthesis of N-(N-Boc-aminoethyl)-N-(o-nitrosulfonyl)Nε-Cbz-L-lysine methyl ester (13)

A solution of Nα-(o-nitrosulfonyl)Nε-Cbz-L-lysine methyl ester (6) (20.0 mmol) was treated as per the procedure of Example 10 to give a 93.7% yield of N-(N-Boc-aminoethyl)-N-(o-nitrosulfonyl)Nε-Cbz-L-lysine methyl ester as a hygroscopic white foam. R$_f$(CH$_2$Cl$_2$/AcOEt 9:1) 0.35. $^1$H NMR: δ1.41 (s, 9H), 1.41–1.65 (m, 4H), 1.70–1.90 (m, 1H), 1.92–2.10 (m, 1H), 3.15–3.47 (m, 6H), 3.54 (s, 3H), 4.76 (dd, 1H, J=10.0, 4.6 Hz), 5.06 (br s, 2H), 5.09 (s, 2H), 7.26–7.37 (m, 5H), 7.53–7.70 (m, 3H), 7.99–8.04 (m, 1H). $^{13}$C NMR: δ23.25, 28.26, 28.81, 29.28, 40.38, 40.75, 45.65, 52.19, 60.65, 66.27, 79.29, 123.85, 127.83, 128.34, 130.85, 131.46, 131.82, 133.81, 136.69, 147.90, 155.98, 156.48, 171.81. Anal Calcd for C$_{28}$H$_{38}$N$_4$O$_{10}$S (0.4 CHCl$_3$): C, 50.88; H, 5.73; N, 8.36. Found: C, 51.19; H, 5.70; N, 8.51.

EXAMPLE 14

Mitsunobu Coupling, Synthesis of N-(N-Boc-aminoethyl)-N-(o-nitrosulfonyl)Nε-Cbz-D-lysine methyl ester (14)

A solution of Nα-(o-nitrosulfonyl)Nε-Cbz-D-lysine methyl ester (14) (20.0 mmol) was treated as per the procedure of Example 10 to give a 95.7% yield N-(N-Boc-aminoethyl)-N-(o-nitrosulfonyl)Nε-Cbz-D-lysine methyl ester as a colorless syrup.

EXAMPLE 15

Mitsunobu Coupling, Synthesis of N-(N-Boc-aminoethyl)-N-(o-nitrosulfonyl)L-phenylalanine methyl ester (15)

A solution of Nα-(o-nitrosulfonyl)L-phenylalanine methyl ester (8) (20.0 mmol) was treated as per the procedure of Example 10 to give a 92.9% yield of N-(N-Boc-aminoethyl)-N-(o-nitrosulfonyl)L-phenylalanine methyl ester as a white foam. R$_f$(CH$_2$Cl$_2$/hexanes/AcOEt 60:30:1) 0.18. $^1$H NMR: δ1.44 (s, 9H), 3.11 (dd, 1H, J=14.7, 8.8 Hz), 3.26–3.56 (m, 5H), 3.57 (s, 3H), 4.92 (t, 1H, J=6.8 Hz), 5.02 (t, 1H, J=5.5 Hz), 7.19–7.28 (m, 5H), 7.52–7.80 (m, 4H). $^{13}$C NMR: δ28.43, 36.04, 40.55, 52.46, 61.34, 79.38, 124.09, 127.04, 128.65, 128.99, 129.30, 130.73, 131.75, 132.23, 133.91, 136.12, 148.12, 156.05, 171.02. Anal Calcd for C$_{23}$H$_{29}$N$_3$O$_8$S (0.25 CHCl$_3$): C, 51.96; H, 5.45; N, 7.82. Found: C, 51.82; H, 5.45; N, 7.61.

EXAMPLE 16

Mitsunobu Coupling, Synthesis of N-(N-Boc-aminoethyl)-N-(o-nitrosulfonyl)-O-(tert-butydiphenylsilyl)-L-tyrosine methyl ester (16)

A solution of Nα-(o-nitrosulfonyl)O-(tert-butyldiphenylsilyl)-L-tyrosine methyl ester (9) (20.0 mmol) was treated as per the procedure of Example 10 to give a 91.7% yield of N-(N-Boc-aminoethyl)-N-(o-nitrosulfonyl)-O-(tert-butydiphenylsilyl)-L-tyrosine methyl ester as a yellow foam. R$_f$(/hexanes/AcOEt 2:1) 0.35 $^1$H NMR: δ1.08 (s, 9H), 1.43 (s, 9H), 2.95 (dd, 1H, J=14.7, 8.8 Hz), 3.19–3.31 (m, 3H), 3.43–3.52 (m, 2H), 3.53 (s, 3H), 4.77 (t, 1H, J=7.3 Hz), 4.94 (t, J=4.5 Hz), 6.61–6.66 (m, 2H), 6.90–6.95 (m, 2H), 7.32–7.81 (m, 14H). $^{13}$C NMR: δ19.50, 26.61, 26.47, 35.39, 40.62, 45.68, 52.35, 61.30, 79.42, 119.94, 124.08, 127.68, 127.84, 128.37, 129.80, 130.02, 130.91, 131.59, 132.46, 132.94, 133.73, 135.60, 148.17, 154.63, 156.01, 171.19. Anal Calcd for C$_{39}$H$_{47}$N$_3$O$_9$SSi (0.6 H$_2$O): C, 60.64; H, 6.25; N, 5.44. Found: C, 60.67; H, 6.09; N, 5.28.

EXAMPLE 17

Removal of the o-nitrosulfonyl Group, Synthesis of N-(N-Boc-aminoethyl)glycine methyl ester (17)

To a suspension of N-(N-Boc-aminoethyl)-N-(o-nitrosulfonyl)glycine methyl ester (10) (10.0 mmol) and K$_2$CO$_3$ (30.0 mmol) in DMF (100 mL) was added PhSH (12.0 mmol) at 23° C. The mixture was stirred at 23° C. for 14 hours. The resultant mixture was diluted with AcOEt (500 mL) and washed with $H_2O$ (2×250 mL). The organic phase was dried over ($MgSO_4$) and concentrated in vacuo. The resultant residue was purified by silica gel flash column chromatography. The polarity of the eluting solvent mixture was adjusted according to the $R_f$ value of the product. The product fractions were concentrated and dried to give a 98.0% yield of N-(N-Boc-aminoethyl)glycine methyl ester as a colorless syrup. Boiling point (bp): 106–110° C./0.3 torr (Kugelrohr). (Dueholm, K. L., et al., *Org. Prep. Proceed. Int.*, 1993, 25, 457, reported a pure sample that was purified at 100° C./0.2 torr(Kugelrohr).

EXAMPLE 18

Removal of the o-nitrosulfonyl Group, Synthesis of N-(N-Boc-aminoethyl)L-alanine methyl ester (18)

A suspension of N-(N-Boc-aminoethyl)-N-(o-nitrosulfonyl)L-alanine methyl ester (11) (10.0 mmol) and $K_2CO_3$ (30.0 mmol) in DMF (100 mL) was treated with thiophenyl (12.0 mmol) as per the procedures of Example 17 to give a 90.2% yield of N-(N-Boc-aminoethyl)L-alanine methyl ester as a colorless syrup. $R_f$(CHCl$_3$/MeOH 9:1) 0.45. $^1$H NMR: δ1.29 (d, 3H, J=7.0 Hz), 1.44 (s, 9H), 1.67 (br s, 1H), 2.58 (ddd, 1H, J=11.9, 6.7, 5.3 Hz), 2.75 (ddd, 1H, J=11.9, 6.5, 4.8 Hz), 3.18 (m, 2H), 3.33 (q, 1H, J=7.0 Hz), 3.72 (s, 3H), 4.98 (br s, 1H). $^{13}$C NMR: δ18.80, 28.25, 40.30, 47.10, 51.59, 56.09, 78.81, 156.01, 175.88. Anal Calcd for $C_{11}H_{22}N_2O_4$: C, 53.66; H, 8.94; N, 11.30. Found: C, 53.94; H, 8.74; N,10.95.

EXAMPLE 19

Removal of the o-nitrosulfonyl Group, Synthesis of N-(N-Boc-aminoethyl)L-leucine methyl ester (19)

A suspension of N-(N-Boc-aminoethyl)-N-(o-nitrosulfonyl)L-leucine methyl ester (12) (10.0 mmol) and $K_2CO_3$ (30.0 mmol) in DMF (100 mL) was treated with PhSH (12.0 mmol) as per the procedures of Example 17 to give a 93.4% yield of N-(N-Boc-aminoethyl)L-leucine methyl ester as a colorless syrup. $R_f$(CHCl$_3$/MeOH 9:1) 0.66. $^1$H NMR: δ0.89 (d, 3H, J=4.9 Hz), 0.92 (d, 3H, J=4.9 Hz), 1.43 (dd, 2H, J=7.3, 6.8 Hz), 1.59 (br s, 1H, $D_2O$ exchangable), 1.72 (tq, 1H, J=6.8, 4.9 Hz), 2.52 (ddd, 1H, J=12.0, 6.8, 5.1 Hz), 2.74 (ddd, 1H, J=12.0, 6.5, 4.8 Hz), 3.18 (m, 2H), 3.24 (t, 1H, J=7.3 Hz), 3.70 (s, 3H), 4.97 (br s, 1H). $^{13}$C NMR: δ22.11, 22.54, 24.73, 28.26, 40.33, 42.56, 47.32, 51.42, 59.50, 78.81, 155.99, 176.14. Anal Calcd for $C_{14}H_{28}N_2O_4$(0.1 $H_2O$): C, 57.97; H, 9.70; N, 9.66. Found: C, 57.92; H, 9.86; N, 9.66.

EXAMPLE 20

Removal of the o-nitrosulfonyl Group, Synthesis of N-(N-Boc-aminoethyl)-Nε-Cbz-L-lysine methyl ester (20)

A suspension of N-(N-Boc-aminoethyl)-N-(o-nitrosulfonyl)Nε-Cbz-L-lysine methyl ester (13) (10.0 mmol) and $K_2CO_3$ (30.0 mmol) in DMF (100 mL) was treated with PhSH (12.0 mmol) as per the procedures of Example 17 to give a 92.9% yield of N-(N-Boc-amninoethyl)-Nε-Cbz-D-lysine methyl ester as a pale yellow syrup. $R_f$(CHCl$_3$/MeOH 9:1) 0.59. $^1$H NMR: δ1.32–1.65 (m, 6H), 1.44 (s, 9H), 2.53 (ddd, 1H, J=11.8, 6.4, 5.6 Hz), 2.74 (ddd, 1H, J=11.8, 6.4, 4.7 Hz), 3.07–3.23 (m, 5H), 3.71 (s, 3H), 4.86 (br s, 1H), 4.95 (br s, 1H), 5.09 (s, 2H), 7.29–7.36 (m, 5H). $^{13}$C NMR: δ22.91, 28.41, 29.63, 32.95, 40.44, 40.77, 47.46, 51.71, 60.90, 66.49, 79.11, 127.74, 128.02, 128.46, 136.72, 156.08, 156.48, 175.72. Anal Calcd for $C_{22}H_{35}N_3O_6$: C, 60.41; H, 8.01; N, 9.61. Found: C, 60.27; H, 7.88; N,9.99.

EXAMPLE 21

Removal of the o-nitrosulfonyl Group, Synthesis of N-(N-Boc-aminoethyl)-Nε-Cbz-D-lysine methyl ester (21)

A suspension of N-(N-Boc-aminoethyl)-N-(o-nitrosulfonyl)Nε-Cbz-D-lysine methyl ester (14) (10.0 mmol) and $K_2CO_3$ (30.0 mmol) in DMF (100 mL) was treated with PhSH (12.0 mmol) as per the procedures of Example 17 to give a 83.5% yield of N-(N-Boc-aminoethyl)-Nε-Cbz-D-lysine methyl ester as a colorless syrup.

EXAMPLE 22

Removal of the o-nitrosulfonyl Group, Synthesis of N-(N-Boc-aminoethyl)L-phenylalanine methyl ester (22)

A suspension of N-(N-Boc-aminoethyl)-N-(o-nitrosulfonyl)L-phenylalanine methyl ester (15) (10.0 mmol) and $K_2CO_3$ (30.0 mmol) in DMF (100 mL) was treated with PhSH (12.0 mmol) as per the procedures of Example 17 to give a 93.2% yield of N-(N-Boc-aminoethyl)L-phenylalanine methyl ester as a colorless syrup. $R_f$(hexanes/AcOEt 1:1) 0.07. $^1$H NMR: δ1.43 (s, 9H), 1.64 (br s, 1H, $D_2O$ exchangable), 2.53 (ddd, 1H, J=11.9, 6.6, 5.3 Hz), 2.74 (ddd, 1H, J=11.9, 6.4, 4.9 Hz), 2.92 (ABq then d, 2H, J=13.5, 7.5 Hz), 3.05–3.16 (m, 2H), 3.48 (t, 1H, J=7.5 Hz), 3.66 (s, 3H), 4.83 (br s, 1H), 7.15–7.34 (m, 5H). $^{13}$C NMR: δ28.41, 39.63, 40.18, 47.31, 51.55, 62.46, 78.92, 126.72, 128.41, 129.13, 137.34, 155.99, 174.90. Anal Calcd for $C_{17}H_{26}N_2O_4$: C, 63.35; H, 8.07; N, 8.70. Found: C, 63.16; H, 7.79; N, 8.52.

EXAMPLE 23

Removal of the o-nitrosulfonyl Group, Synthesis of N-(N-Boc-aminoethyl)-O-(tert-butyldiphenylsilyl)-L-tyrosine methyl ester (23)

A suspension of N-(N-Boc-aminoethyl)-N-(o-nitrosulfonyl)-O-(tert-butyldiphenylsilyl)-L-tyrosine methyl ester (16) (10.0 mmol) and $K_2CO_3$ (30.0 mmol) in DMF (100 mL) was treated with PhSH (12.0 mmol) as per the procedures of Example 17 to give a 94.4% yield of N-(N-Boc-aminoethyl)-O-(tert-butyldiphenylsilyl)-L-tyrosine methyl ester as a yellow syrup. $R_f$(CHCl$_3$/MeOH 9:1): 0.39. $^1$H NMR: δ1.09 (s, 9H), 1.43 (s, 9H), 1.60 (br s, 1H, $D_2O$ exchangable), 2.51 (ddd, 1H, J=12.0, 6.5, 5.5 Hz), 2.68 (ddd, 1H, J=12.0, 6.9, 5.5 Hz), 2.79 (d, 2H, J=6.8 Hz), 3.04–3.15 (m, 2H), 3.38 (t, 1H, J=6.8 Hz), 3.57 (s, 3H), 4.86 (br s, 1H), 6.47–6.70 (m, 2H), 6.84–6.90 (m, 2H), 7.31–7.46 (m, 6H), 7.68–7.72 (m, 4H). $^{13}$C NMR: δ19.48, 26.59, 28.47, 38.93, 40.30, 47.42, 51.62, 62.73, 79.13, 119.76, 127.78, 129.68, 129.92, 133.02, 135.58, 154.47, 156.06, 175.02. Anal Calcd for $C_{33}H_{44}N_2O_5Si$ (0.4 CHCl$_3$): C, 64.25; H, 7.12; N, 4.49. Found: C, 64.55; H, 7.43; N, 4.61.

EXAMPLE 24

Shift Lysine PNA Backbone, Synthesis of N-((2S)-N2-Boc-N6-Cbz-2,6-diaminohexyl)glycine methyl ester by Mitsunobu Coupling (24)

Boc-L-Lysinol(Z) (35.0 g, 13.7 mmol; Advanced ChemTech, CAT# BK4376) and N-(o-nitrosulfonyl)glycine methyl ester 3a (31.5 g, 114.8 mmol) was treated as per the procedures of Example 10 to give 45.4 g (76.3%) of the coupled product as a brown syrup. $R_f(CH_2Cl_2/AcOEt\ 9:1)$: 0.25. $^1H$ NMR: δ1.25–1.50 (m, 6H), 1.33 (s, 9H), 3.18 (dd, 2H, J=12.2, 6.2 Hz), 3.55–3.62 (m, 2H), 3.62 (s, 3H), 3.73 (m, 1H), 4.27 (ABq, 2H, J=18.2 Hz), 4.63 (d, 1H, J=9.1 Hz), 4.86 (t, 1H, J=4.9 Hz), 5.09 (s, 2H), 7.30–7.38 (m, 5H), 7.58–7.71 (m, 3H), 7.99–8.04 (m, 1H). $^{13}C$ NMR: δ22.80, 28.34, 29.60, 32.18, 40.62, 47.76, 47.91, 51.93, 52.22, 66.64, 79.69, 124.16, 128.03, 128.52, 130.74, 131.71, 133.30, 133.62, 136.69, 148.01, 155.99, 156.54, 169.19. Anal Calcd for $C_{28}H_{38}N_4O_{10}S$: C, 54.02; H, 6.11; N, 9.00. Found: C, 53.98; H, 6.19; N, 8.82.

The coupled product was desulfonylated as per the procedures of Example 17 to give 28.1 g (88.9%) of N-((2S)-N2-Boc-N6-Cbz-2,6-diaminohexyl)glycine methyl ester as a yellow syrup. $R_f(CH_2Cl_2/AcOEt\ 9:1)$: 0.08. $^1H$ NMR: δ1.30–1.55 (m, 6H), 1.41 (s, 9H), 1.89 (s, 1H, $D_2O$ exchangable), 2.62 (m, 2H), 3.18 (dd, 2H J=12.6, 6.4 Hz), 3.40 (ABq, 2H, J=18.0 Hz), 3.62 (m, 1H), 3.71 (s, 3H), 4.76 (d, 1H, J=6.7 Hz), 4.86 (t, 1H, J=4.9 Hz), 5.08 (s, 2H), 7.28–7.38 (m, 5H). $^{13}C$ NMR: δ22.94, 28.42, 29.65, 32.83, 40.78, 50.24, 50.77, 51.76, 53.03, 66.60, 79.25, 127.68, 128.06, 128.50, 136.72, 155.96, 156.52, 162.94. Anal Calcd for $C_{22}H_{35}N_3O_6$ (0.25 $CHCl_3$): C, 57.16; H, 7.60; N, 8.99. Found: C, 56.86; H, 7.90; N, 8.83.

EXAMPLE 25

Shift Lysine PNA Backbone, Synthesis of N-((2R)-N2-Boc-N6-Cbz-2,6-diaminohexyl)glycine methyl ester (25)

Boc-D-Lysinol(Z) (20.0 g, 54.6 mmol; Advanced ChemTech, CAT# BK5376) and 3, was treated as per the procedures of Example 24 to give 14.7 g (61.1%) of N-((2R)-N2-Boc-N6-Cbz-2,6-diaminohexyl)glycine methyl ester as a yellow syrup.

EXAMPLE 26

N-(2-nitrobenzenesulfonyl)-D-glutamic acid, α-allyl-γ-benzyl diester (26)

A solution of Boc-D-glutamic acid α-allyl-γ-benzyl diester (2, Example 2) (10.0 g, 26.6 mmol) in $CF_3CO_2H$ (25 mL) was stirred at 23° C. for 2 hours. Removal of the solvent at reduced pressure gave 10.5 g (~100%) of unprotected amine (26a) as a $CF_3CO_2H$ salt. To the unprotected amine (26a) in $CH_2Cl_2$/diisopropylethyl amine (9:1, 200 mL) was added 2-nirtrobenzensulfonyl chloride (8.7 g, 39.2 mmol) in $CH_2Cl_2$ (20 mL) at 0° C. (exothermic) over 0.2 hour period. The mixture was warmed up to 23° C. and stirred for 4 hours. The solvent was removed and the residue was dissolved in AcOEt (250 mL), washed with $H_2O$ (2×200 mL) and brine (50 mL) The organic phase was separated, dried over $MgSO_4$ and filtered. The filtrate was concentrated at reduced pressure and the residue was purified by silica gel flash column chromatography to give a 7.2 g (58.7%) of N-(2-nitrobenzenesulfonyl)-D-glutamic acid, α-allyl-γ-benzyl diester as a brown syrup. $R_f$(hexanes/AcOEt 1:1): 0.42. $^1H$ NMR: δ1.91–2.10 (m, 1H), 2.20–2.37 (m, 1H), 2.56–2.64 (m, 2H), 4.24 (ddd, 1H, J=8.8, 6.8, 4.9 Hz), 4.35 (m, 2H), 5.12–5.14 (m, 1H), 5.14 (s, 2H), 5.21 (m, 1H), 5.56–5.76 (m, 1H), 7.35 (s, 5H), 7.66–7.77 (m, 3H), 7.93–8.06 (m, 1H). $^{13}C$ NMR: δ28.13, 28.88, 56.07, 66.40, 66.62, 79.93, 119.39, 125.69, 128.32, 128.62, 130.56, 130.93, 133.05, 135.80, 147.63, 1710.30, 172.31.

EXAMPLE 27

Synthesis of N-(2-Aminoethyl)-D-Glutamic Acid, α-Allyl-γ-Benzyl Diester (27)

N-Boc-aminoethanol (1.6 g, 9.8 mmol; Aldrich Chemical Company, CAT# 38,202-7) and N-(2-nitrobenzenesulfonyl)-D-glutamic acid, α-allyl-γ-benzyl diester (26) (31.5 g, 114.8 mmol) was treated as per the procedures of Example 10 to give 4.5 g (84.0%) of the Mitsunobu coupled product (27a) as a yellow syrup. 27a: $R_f$(hexanes/AcOEt 9:1) 0.30. $^1H$ NMR δ1.43 (s, 9H), 2.05 (m, 1H), 2.44–2.64 (m, 3H), 3.25–3.53 (m, 4H), 4.45 (dd, 2H, J=5.9, 4.5 Hz), 4.73 (dd, 1H, J=10.0, 3.9 Hz), 5.02 (br t, 1H, J=5.0 Hz), 5.14 (m, 3H), 5.15 (ddd, 1H, J=11.7, 3.0, 2.2 Hz), 5.70 (dddd, 1H, J=11.7, 9.5, 5.9, 4.5 Hz), 7.30–7.39 (m, 5H), 7.54–7.72 (m, 3H), 7.96–8.03 (m, 1H). $^{13}C$ NMR δ25.07, 28.31, 30.45, 40.88, 46.07, 60.22, 66.27, 66.50, 79.34, 119.17, 124.06, 128.25, 128.57, 131.16, 131.73, 131.94, 134.04, 135.85, 148.08, 156.01, 169.83, 172.12.

The coupled product (27a) was desulfonylated as per the procedures of Example 17 to give 3.0 g (96.1%) of N-(2-Aminoethyl)-D-Glutamic Acid, α-Allyl-γ-Benzyl Diester as a colorless syrup. $R_f(CHCl_3/MeOH\ 20:1)$: 0.32. $^1H$ NMR: δ1.44 (s, 9H), 1.76–2.12 (m, 2H), 2.42–2.54 (m, 3H), 2.76 (ddd, 1H, J=11.0, 6.4, 4.7 Hz), 3.10–3.21 (m, 2H), 3.24 (dd, 1H, J=8.5, 5.4 Hz), 4.59 (ddd, 1H, J=5.8, 3.0, 1.3 Hz), 4.62 (ddd, 1H, J=5.7, 2.5, 1.7 Hz), 4.96 (br s, 1H), 5.13 (s, 2H), 5.22 (ddd, 1H, J=10.1, 2.5, 1.3 Hz), 5.31 (ddd, 1H, J=17.4, 3.0, 1.7 Hz), 5.91 (dddd, 1H, J=17.4, 10.1, 5.8, 5.7 Hz), 7.35 (s, 5H). $^{13}C$ NMR: δ28.43, 30.92, 40.40, 47.46, 60.35, 65.47, 66.25, 79.02, 118.75, 128.25, 128.54, 131.84, 135.97, 156.04, 172.90, 174.41.

EXAMPLE 28

Synthesis of Protected Monomers

According to the procedure of Example 24, commercially available alcohol derivatives of selected amino acids (only the L isomers are shown) are reacted with sulfonylated amino acids to give compounds having formula (1) wherein one of $R_5$ or $R_6$ is H and the other is the corresponding side chain of the particular amino acid used. The amino acids in the representative list below have side chain functional groups protected (available in protected form from Advanced ChemTech).

| Amino Acid | Cat. # |
| --- | --- |
| Boc-alinol | BA4119 |
| Boc-cyseinol (p-Me-Bzl) | BC4146 |
| Boc-histidinol (Tox) | BH4316 |
| Boc-isoleucinol | BI4344 |
| Boc-leucinol | BL4369 |
| Boc-methioninol | BM4418 |
| Boc-phenylalaninol | BF4444 |
| Boc-prolinol | BP4451 |
| Boc-serinol (Bzl) | BS4494 |
| Boc-threoninol (Bzl) | BT4525 |
| Boc-tryptophanol | BW4540 |
| Boc-tyrosinol (2,6-$Cl_2$-Bz) | BY4576 |
| Boc-valinol | BV4594 |

The sulfonylated amino acid is selected from glycine, L-alanine, L-leucine, D-glutamic acid, L-phenylalanine, L-tyrosine, L-lysine and D-lysine. All of these sulfonylated/protected amino acids were synthesized in the examples above.

Various modifications of the invention, in addition to those described herein, will be apparent to those skilled in the art from the foregoing description. Such modifications are intended to fall within the scope of the appended claims.

What is claimed is:

1. A method for preparing a compound of formula (I):

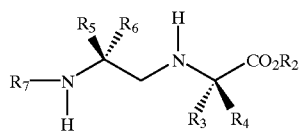
(I)

comprising the steps of providing an amine of formula (II):

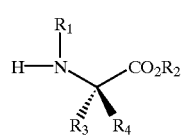
(II)

and contacting said amine with an alcohol of formula (III):

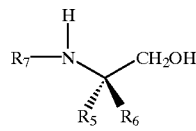
(III)

for a time and under conditions sufficient to effect dehydrative coupling thereof, wherein:

$R_1$ is a first amine protecting group;
$R_2$ is a carboxyl protecting group;
one of $R_3$ and $R_4$ is H and the other of $R_3$ and $R_4$ is $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, an amino acid side chain, a polyalkyl glycol, $C_7$–$C_{14}$ aralkyl or substituted aralkyl; or a substituted or unsubstituted nitrogen, sulfur or oxygen containing heterocycle; and where said substitutions are selected from hydroxyl, alkoxy, alcohol, benzyl, phenyl, nitro, thiol, thioalkoxy, halogen, alkyl, aryl, alkenyl, alkynyl, amidinyl, keto, carbonyl, amido, carbocylic acid ester or guanidinyl;
one of $R_5$ and $R_6$ is H and the other of $R_5$ and $R_6$ is $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, an amino acid side chain, a polyalkyl glycol, $C_7$–$C_{14}$ aralkyl or substituted aralkyl; or a substituted or unsubstituted nitrogen, sulfur or oxygen containing heterocycle; and where said substitutions are selected from hydroxyl, alkoxy, alcohol, benzyl, phenyl, nitro, thiol, thioalkoxy, halogen, alkyl, aryl, alkenyl, alkynyl, amidinyl, keto, carbonyl, amido, carbocylic acid ester or guanidinyl; and
$R_7$ is a second amine protecting group.

2. A method of claim 1 wherein said contacting is effected in an aprotic solvent.

3. A method of claim 1 wherein said contacting is effected in the presence of triaryl phosphine.

4. A method of claim 1 wherein said contacting is effected in the presence of dialkyl azodicarboxylate.

5. A method of claim 1 further comprising the steps of:
providing an amino acid;
appending a carboxyl protecting group to said amino acid, thereby producing a carboxyl-protected amino acid derivative;
appending an amine protecting group to said carboxyl protected amino acid derivative, thereby producing a compound having formula (II).

6. A method of claim 1 further comprising the steps of:
providing an amino acid;
appending an amine protecting group to said amino acid, thereby producing a amine-protected amino acid derivative;
reducing said amine-protected amino acid derivative, thereby producing a compound having formula (III).

7. A compound of formula (I):

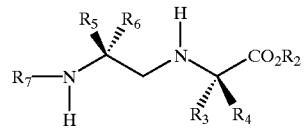
(I)

wherein:
$R_2$ is a carboxyl protecting group;
one of $R_3$ and $R_4$ is H and the other of $R_3$ and $R_4$ is $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, an amino acid side chain, a polyalkyl glycol, $C_7$–$C_{14}$ aralkyl or substituted aralkyl; or a substituted or unsubstituted nitrogen, sulfur or oxygen containing heterocycle; and where said substitutions are selected from hydroxyl, alkoxy, alcohol, benzyl, phenyl, nitro, thiol, thioalkoxy, halogen, alkyl, aryl, alkenyl, alkynyl, amidinyl, keto, carbonyl, amido, carbocylic acid ester or guanidinyl;
one of $R_5$ and $R_6$ is H and the other of $R_5$ and $R_6$ is $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, an amino acid side chain, a polyalkyl glycol, $C_7$–$C_{14}$ aralkyl or substituted aralkyl; or a substituted or unsubstituted nitrogen, sulfur or oxygen containing heterocycle; and where said substitutions are selected from hydroxyl, alkoxy, alcohol, benzyl, phenyl, nitro, thiol, thioalkoxy, halogen, alkyl, aryl, alkenyl, alkynyl, amidinyl, keto, carbonyl, amido, carbocylic acid ester or guanidinyl; and
$R_7$ is an amine protecting group.

8. A compound of claim 7 having at least 75% stereochemical purity with respect to a Cα-position thereof.

9. A compound of claim 7 having greater then 99% stereochemical purity with respect to a Cα-position thereof.

10. A compound of claim 8 having at least 75% stereochemical purity with respect to a Cβ-position thereof.

11. A compound of claim 7 having R,S configuration with respect to Cα- and Cβ-positions thereof.

12. A compound of claim 7 having R,R configuration with respect to Cα- and Cβ-positions thereof.

13. A compound of claim 7 having S,R configuration with respect to Cα- and Cβ-positions thereof.

14. A compound of claim 7 having S,S configuration with respect to Cα- and Cβ-positions thereof.

15. A compound of claim 7 wherein one of $R_3$ and $R_4$ is HO—$CH_2$—, HO—$C_6H_5$—$CH_2$—, $HO_2C$—CH($NH_2$)—$CH_2$—S—S—$CH_2$—, HO—$CH_2$—$CH_2$—, $HCO_2$—$CH_2$—$CH_2$—, $H_2N$—C(NH)—NH—$CH_2$—$CH_2$—$CH_2$—, $H_2N$—C(O)—NH—$CH_2$—$CH_2$—$CH_2$—, $H_2N$—$CH_2$—$CH_2$—$CH_2$— or p—HO—m—HO—$C_6H_4$—$CH_2$—.

16. A compound of claim 7 wherein one of $R_5$ and $R_6$ is HO—$CH_2$—, HO—$C_6H_5$—$CH_2$—, $HO_2C$—CH($NH_2$)—$CH_2$—S—S—$CH_2$—, HO—$CH_2$—$CH_2$—, $HCO_2$—$CH_2$—$CH_2$—, $H_2N$—C(NH)—NH—$CH_2$—$CH_2$—$CH_2$—, $H_2N$—C(O)—NH—$CH_2$—$CH_2$—$CH_2$—, $H_2N$—$CH_2$—$CH_2$—$CH_2$— or p—HO—m—HO—$C_6H_4$—$CH_2$—.

17. A compound having formula (IV):

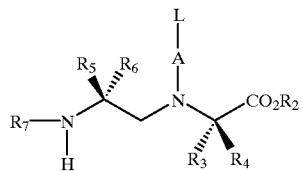

(IV)

wherein:

$R_2$ is a carboxyl protecting group;

one of $R_3$ and $R_4$ is H and the other of $R_3$ and $R_4$ is $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, an amino acid side chain, a polyalkyl glycol, $C_7$–$C_{14}$ aralkyl or substituted aralkyl; or a substituted or unsubstituted nitrogen, sulfur or oxygen containing heterocycle; and where said substitutions are selected from hydroxyl, alkoxy, alcohol, benzyl, phenyl, nitro, thiol, thioalkoxy, halogen, alkyl, aryl, alkenyl, alkynyl, amidinyl, keto, carbonyl, amido, carbocylic acid ester or guanidinyl;

one of $R_5$ and $R_6$ is H and the other of $R_5$ and $R_6$ is $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, an amino acid side chain, a polyalkyl glycol, $C_7$–$C_{14}$ aralkyl or substituted aralkyl; or a substituted or unsubstituted nitrogen, sulfur or oxygen containing heterocycle; and where said substitutions are selected from hydroxyl, alkoxy, alcohol, benzyl, phenyl, nitro, thiol, thioalkoxy, halogen, alkyl, aryl, alkenyl, alkynyl, amidinyl, keto, carbonyl, amido, carbocylic acid ester or guanidinyl;

$R_7$ is an amine protecting group;

L is selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, and heterocyclic moieties, reporter ligands, wherein amino groups are, optionally, protected by amino protecting groups;

A is a group of formula (IIa)–(IId):

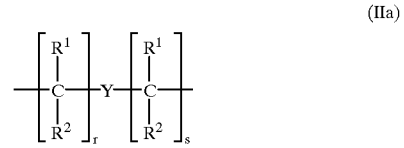

(IIa)

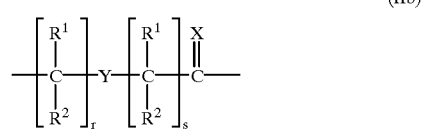

(IIb)

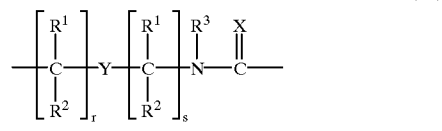

(IIc)

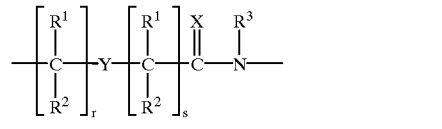

(IId)

where:

X is O, S, Se, $NR^3$, $CH_2$ or $C(CH_3)_2$;

Y is a single bond, O, S or $NR^4$ where $R^4$ is as described above;

each r and s is zero or an integer from 1 to 5;

each $R_1$ and $R_2$ is independently selected from the group consisting of hydrogen, ($C_1$–$C_4$)alkyl which may be hydroxy- or alkoxy- or alkylthio-substituted, hydroxy, alkoxy, alkylthio, amino and halogen; and $R^3$ is selected from the group consisting of hydrogen, ($C_1$–$C_4$)alkyl, hydroxy- or alkoxy- or alkylthio-substituted ($C_1$–$C_4$)alkyl, hydroxy, alkoxy, alkylthio and amino.

18. A compound of claim 17 having at least 75% stereochemical purity with respect to a Cα-position thereof.

19. A compound of claim 17 having greater then 99% stereochemical purity with respect to a Cα-position thereof.

20. A compound of claim 18 having at least 75% stereochemical purity with respect to a Cβ-position thereof.

21. A compound of claim 17 having R,S configuration with respect to Cα- and Cβ-positions thereof.

22. A compound of claim 17 having R,R configuration with respect to Cα- and Cβ-positions thereof.

23. A compound of claim 17 having S,R configuration with respect to Cα- and Cβ-positions thereof.

24. A compound of claim 17 having S,S configuration with respect to Cα- and Cβ-positions thereof.

25. A compound of claim 17 wherein one of $R_3$ and $R_4$ is HO—$CH_2$—, HO—$C_6H_5$—$CH_2$—, $HO_2C$—CH($NH_2$)—$CH_2$—S—S—$CH_2$—, HO—$CH_2$—$CH_2$—, $HCO_2$—$CH_2$—$CH_2$—, $H_2N$—C(NH)—NH—$CH_2$—$CH_2$—$CH_2$—, $H_2N$—C(O)—NH—$CH_2$—$CH_2$—$CH_2$—, $H_2N$—$CH_2$—$CH_2$—$CH_2$— and p—HO—m—HO—$C_6H_4$—$CH_2$—.

26. A compound of claim 17 wherein one of $R_5$ and $R_6$ is HO—$CH_2$—, HO—$C_6H_5$—$CH_2$—, $HO_2C$—CH($NH_2$)—$CH_2$—S—S—$CH_2$—, HO—$CH_2$—$CH_2$—, $HCO_2$—$CH_2$—$CH_2$—, $H_2N$—C(NH)—NH—$CH_2$—$CH_2$—$CH_2$—, $H_2N$—C(O)—NH—$CH_2$—$CH_2$—$CH_2$—, $H_2N$—$CH_2$—$CH_2$—$CH_2$— or p—HO—m—HO—$C_6H_4$—$CH_2$—.

27. A compound of claim 17 wherein A has formula (IIa).

28. A compound of claim 17 wherein A has formula (IIb).
29. A compound of claim 17 wherein A has formula (IIc).
30. A compound of claim 17 wherein A has formula (IId).
31. A compound of claim 17 wherein L is a nucleobase.
32. A method for preparing a compound of formula (I):

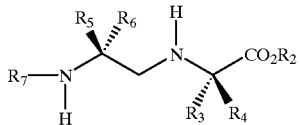
(I)

comprising the steps of providing an amine of formula (II):

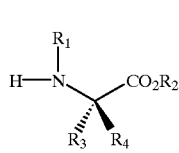
(II)

and contacting said amine with an alcohol of formula (III):

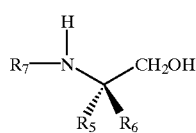
(III)

for a time and under conditions sufficient to effect dehydrative coupling thereof, wherein:
$R_1$ is a first amine protecting group;
$R_2$ is a carboxyl protecting group;
each $R_3$, $R_4$, $R_5$, and $R_6$ is, independently, H, $C_2$–$C_{10}$ alkyl or substituted alkyl, $C_2$–$C_{10}$ alkenyl or substituted alkenyl, $C_2$–$C_{10}$ alkynyl or substituted alkynyl, $C_4$–$C_7$ carbocylo alkyl or alkenyl, an ether having 2 to 10 carbon atoms and 1 to 4 oxygen or sulfur atoms, a polyalkyl glycol, $C_7$–$C_{14}$ aralkyl or substituted aralkyl; or a substituted or unsubstituted nitrogen, sulfur or oxygen containing heterocycle; and where said substitutions are selected from hydroxyl, alkoxy, alcohol, benzyl, phenyl, nitro, thiol, thioalkoxy, halogen, alkyl, aryl, alkenyl, alkynyl, amidinyl, keto, carbonyl, amido, carbocylic acid ester or guanidinyl; and
$R_7$ is a second amine protecting group.

33. A method of claim 32 wherein said contacting is effected in an aprotic solvent.
34. A method of claim 32 wherein said contacting is effected in the presence of triaryl phosphine.
35. A method of claim 32 wherein said contacting is effected in the presence of dialkyl azodicarboxylate.
36. A method of claim 32 further comprising the steps of:
   providing an amino acid;
   appending a carboxyl protecting group to said amino acid, thereby producing a carboxyl-protected amino acid derivative;
   appending an amine protecting group to said carboxyl protected amino acid derivative, thereby producing a compound having formula (II).
37. A method of claim 32 further comprising the steps of:
   providing an amino acid;
   appending an amine protecting group to said amino acid, thereby producing a amine-protected amino acid derivative;
   reducing said amine-protected amino acid derivative, thereby producing a compound having formula (III).
38. A method of claim 32 wherein $R_5$ and $R_6$ and one of $R_3$ and $R_4$ is H and the other of $R_3$ and $R_4$ is not H.
39. A method of claim 32 wherein $R_3$ and $R_4$ and one of $R_5$ and $R_6$ is H and the other of $R_5$ and $R_6$ is not H.
40. A method of claim 32 wherein the amine of formula II is chiral.
41. A method of claim 32 wherein the alcohol of formula III is chiral.
42. A method of claim 41 wherein the amine of formula II is chiral.

* * * * *

UNITED STATES PATENT AND TRADEMARK OFFICE
CERTIFICATE OF CORRECTION

PATENT NO. : 6,015,887
DATED : January 18, 2000
INVENTOR(S) : Kelly Teng

It is certified that error appears in the above-identified patent and that said Letters Patent is hereby corrected as shown below:

Column 5,
Line 35, please add -- A is a group of formula (IIa) - (IId) -- (over top diagram)

Column 10,
Lines 48 and 49, please delete "D" and insert therefor -- $_D$ --

Column 17,
Line 50, please delete "nirtrobenzensulfonyl" and insert therefor -- nitrobenzensulfonyl --

Column 21,
Line 10, please add another -- $CH_2$ -- before the word "or"

Column 22,
Line 60, please delete "and" and insert therefor -- or --

Signed and Sealed this

Thirteenth Day of August, 2002

Attest:

JAMES E. ROGAN
Attesting Officer   Director of the United States Patent and Trademark Office